(12) United States Patent
Zielinski

(10) Patent No.: US 6,831,098 B1
(45) Date of Patent: Dec. 14, 2004

(54) HESPERETIN PRO-FORMS WITH ENHANCED BIOAVAILABLILITY

(75) Inventor: Jan E. Zielinski, Vista, CA (US)

(73) Assignee: Zielinski Laboratory, Vista, CA (US)

( * ) Notice: Subject to any disclaimer, the term of this patent is extended or adjusted under 35 U.S.C. 154(b) by 0 days.

(21) Appl. No.: 09/890,479

(22) PCT Filed: Jan. 26, 2000

(86) PCT No.: PCT/US00/01923

§ 371 (c)(1), (2), (4) Date: Feb. 8, 2002

(87) PCT Pub. No.: WO00/44757

PCT Pub. Date: Aug. 3, 2000

Related U.S. Application Data

(60) Provisional application No. 60/118,198, filed on Feb. 1, 1999, and provisional application No. 60/117,567, filed on Jan. 27, 1999.

(51) Int. Cl.[7] .............................................. A61K 31/352
(52) U.S. Cl. ........................ 514/457; 549/220; 549/403
(58) Field of Search ........................... 514/457; 549/220, 549/403

(56) References Cited

U.S. PATENT DOCUMENTS 5,587,176 A * 12/1996 Warren et al.

* cited by examiner

Primary Examiner—Joseph K. McKane
Assistant Examiner—Sonya Wright
(74) Attorney, Agent, or Firm—Cray Cary Ware & Freidenrich, LLP

(57) ABSTRACT

A hesperitin pro-form is provided. The invention provides both a hydrophilic and lipophilic hesperetin pro-form. A pharmaceutical composition is provided which is suitable for topical or oral administration in an individual, the composition comprising a hydrophilic hesperetin pro-form and a pharmaceutically acceptable carrier. A pharmaceutical composition is also provided which is suitable for topical or oral administration in an individual, the composition including a lipophilic hesperetin pro-form and a pharmaceutically acceptable carrier. A method is provided for treating a subject having or at risk of having a cell proliferative disorder, including administering to the subject a therapeutically effective amount of a hesperetin pro-form.

8 Claims, No Drawings

HESPERETIN PRO-FORMS WITH ENHANCED BIOAVAILABLILITY

This application claims benefit of provisional applications No. 60/117,567 filed Jan. 27, 1999 and No. 60/118,198 filed Feb. 1, 1999.

FIELD OF THE INVENTION

This invention relates generally to the field of bioflavanoids, and more specifically to forms of bioflavanoids that increase their bioavailability, and to the use of these compounds for the treatment of disease.

BACKGROUND OF THE INVENTION

Hesperidin and the a glycone of hesperidin, hesperetin, are flavonoids found in lemons, grapefruits, tangerines, and oranges, and have the following structures:

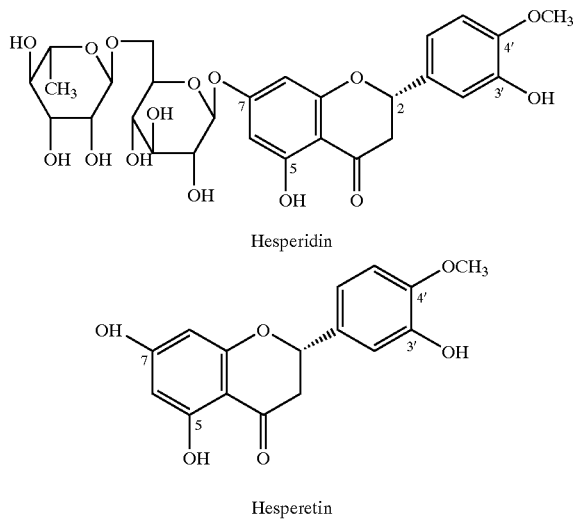

Hesperidin

Hesperetin

Flavonoids from citrus fruits, known as bioflavonoids exhibit beneficial effects, suppressing oxidative stress, inhibit breast cancer and have anti-inflammatory function.

Hesperidin has been used for the prevention and treatment of cerebral anemia, and pelioma. Recently has been found that hesperidin and hesperetin are effective inhibitors of 3-hydroxy-3-methylglutaryl CoA (U.S. Pat. No. 5,763,414, herein incorporated by reference). Moreover, hesperetin has topical application for sebum control and treatment of acne in mammalian skin and scalp (U.S. Pat. No. 5,587,176, herein incorporated by reference).

The bioavailability of flavonoids is an important problem in physiological effects, statistically; less than 20% of administered flavonoid is absorbed to blood which subsequently is metabolized to glucuronides and sulfates. Only free flavonoids without sugar molecule, the so-called aglycones are able to pass through the gut wall. Hydrolysis of flavonoid glycosides only occurs in the colon by microorganisms, which in the same time degrade released flavonoids.

SUMMARY OF THE INVENTION

A hesperitin pro-form is provided. The invention provides both a hydrophilic and a lipophilic hesperetin pro-form.

A pharmaceutical composition is provided which is suitable for topical or oral administration in an individual, the composition comprising a hydrophilic hesperetin pro-form and a pharmaceutically acceptable carrier. A pharmaceutical composition is also provided which is suitable for topical or oral administration in an individual, the composition including a lipophilic hesperetin pro-form and a pharmaceutically acceptable carrier.

A method is provided for treating a subject having or at risk of having a cell proliferative disorder, including administering to the subject a therapeutically effective amount of a hesperetin pro-form.

A method is also provided for decreasing oxidative stress in a subject having a disorder associated with oxidative stress, including administering to the subject a therapeutically effective amount of a hesperitin pro-form.

A method is further provided for treating a subject having or at risk of having a disorder associated with sebacous gland activity, including administering to the subject a therapeutically effective amount of a hesperetin pro-form.

A method is provided for treating a subject having or at risk of having a cardiovascular disorder, including administering to the subject a therapeutically effective amount of a hesperetin pro-form.

DESCRIPTION OF THE PREFERRED EMBODIMENTS

It must be noted that as used herein and in the appended claims, the singular forms "a," "and," and "the" include plural referents unless the context clearly dictates otherwise. Thus, for example, reference to "a cell" includes a plurality of such cells and reference to "the disease" includes reference to one or more diseases and equivalents thereof known to those skilled in the art, and so forth.

Unless defined otherwise, all technical and scientific terms used herein have the same meaning as commonly understood to one of ordinary skill in the art to which this invention belongs. Although any methods, devices and materials similar or equivalent to those described herein can be used in the practice or testing of the invention, the preferred methods, devices and materials are now described.

All publications mentioned herein are incorporated herein by reference in full for the purpose of describing and disclosing the compounds, reagents, and methodologies which are described in the publications which might be used in connection with the presently described invention. The publications discussed above and throughout the text are provided solely for their disclosure prior to the filing date of the present application. Nothing herein is to be construed as an admission that the inventors are not entitled to antedate such disclosure by virtue of prior invention.

A "hesperetin pro-form" is hydrophilic or a lipophilic pro-form of hesperetin of the general formula:

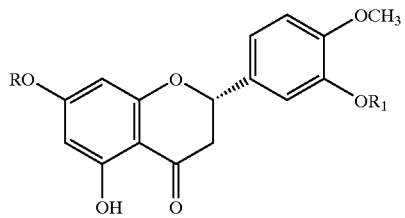

A "hydrophilic hesperetin pro-form" is a compound of the formula indicated above wherein:
R is H and $R_1$ is an organic or an inorganic salt of phosphoric or sulfuric acid residue.

Wherein $R_1$ is H and R is an organic or an inorganic salt of phosphoric or sulfuric acid residue.

A "lipophilic hesperetin pro-form" is a compound of the formula indicated above, wherein:

One of R and $R_1$ is a saturated or unsaturated fatty acid moiety.

One of R and $R_1$ is an acid moiety selected from the group consisting of a straight or branched aliphatic chain, including an alkyl, alkenyl, alkynyl, alkoxyalkyl, alkythioalkyl, aminoalkyl group, including substituted or non-substituted cycloalkyl, and an aromatic group, including aryl, aryalkyl, and substitued derivatives such as where a ring contains one or more nitrogen, sulfer, or oxygens.

Without being bound by theory, a hesperetin pro-form has increased metabolic resistance and improved absorption as compared to hesperetin. "Metabolic resistance" as used herein refers to a decreased ability of an enzyme, normally found in a metabolic pathway, to degrade the compound, as compared to a control compound. "Improved absorption" as used herein refers to an increased ability of an organism to absorb a compound, via any route (e.g. dermal absorption, intestinal absorption) as compared to a control compound. Methods and compositions of the present invention provide increased bioavailability of hesperetin by converting this flavanone into pro-compound. This is preferably accomplished by attaching leaving group, which can be readily hydrolyzed under physiologic conditions to produce the starting flavanone.

In one embodiment, hydroxyl groups at 7 and 3' positions are converted to carboxylic, phosphoric and sulfuric acid esters. In an in vivo environment, enzymatic or spontaneous hydrolysis of the pro-compounds in gastrointestinal tract or skin, release free hesperetin as a function of time. Kinetics of this process can be controlled by appropriate formulation of the procompounds to decrease metabolic transformation and increase absorption of hesperetin in the target cells.

In other aspect of the invention, the pro-compounds may advantageously be employed therapeutically or prophylactically for variety conditions, provided as a dietary supplement, drug or bioactive component of cosmetics.

The molecule of hesperetin has three hydroxyl groups, which differ from each other with different reactivity to acylating reagent. High reactivity of 7-hydroxyl group made possible direct formation of hesperetin-7-esters using activated carboxylic acids or acyl chlorides at the presence of base. Synthesis of hesperetin-3'-eters, required prior esterification of 3'-OH conversion of 7-OH group to benzylformyl or t-butyldimethylsilyl derivatives.

Pharmaceutical Compositions

The invention also contemplates various pharmaceutical compositions containing a hesperetin pro-form that are effective in treating a variety of disorders. These disorders include "cell proliferative disorders", "disorders associated with oxidative stress", "skin disorders", and "cardiovascular disorders".

The term "neoplasia" refers to a disease of inappropriate cell proliferation. This derangement is most evident clinically when tumor tissue bulk compromises the function of vital organs. The term "cell proliferative disorder" denotes malignant as well as nonmalignant cell populations which often appear to differ from the surrounding tissue both morphologically and genotypically. Malignant cells (i.e., tumors or cancer) develop as a result of a multistep process. Concepts describing normal tissue growth are applicable to malignant tissue because normal and malignant tissues can share similar growth characteristics, both at the level of the single cell and at the level of the tissue. Tumors are as much a disease of disordered tissue growth regulation as of disordered cellular growth regulation. The growth characteristics of tumors are such that new cell production exceeds cell death; a neoplastic event tends to produce an increase in the proportion of stem cells undergoing self-renewal and a corresponding decrease in the proportion progressing to maturation (McCulloch, E. A., et al., 1982, "The contribution of blast cell properties to outcome variation in acute myeloblastic leukemia (AML)," *Blood* 52:601–608). In one embodiment, the cells treated by the method of the invention are neoplastic cells.

The term cardiovascular disorder refers to any coronary or cardio-circular disease, including atherosclerosis and hypercholesterolemia.

The term "disorder associated with sebaceous gland activity" refers to a disorder of the pilosebaceous glands of the mammalian skin and scalp. Examples are disorders of sebum secretin such as acne. "Acne" is a pilosebaceous disease characterized by comedo, papules, inflamed nodules and superficial pus-filled cysts. The course and severity of the disease is determined by the interaction between hormones, keratinization, sebum formation and bacteria. The term "treating sebaceous gland activity", as used herein means preventing, retarding, and/or arresting the production of sebum. The tem "treating acne" refers to preventing, retarding, and/or arresting the process of acne formation.

The pharmaceutical compositions according to the invention are prepared by bringing a pro-form of hesperetin of the present invention into a form suitable for administration (e.g., a pharmaceutically acceptable carrier) to a subject using carriers, excipients and additives or auxiliaries. Frequently used carriers or auxiliaries include magnesium carbonate, titanium dioxide, lactose, mannitol and other sugars, talc, milk protein, gelatin, starch, vitamins, cellulose and its derivatives, animal and vegetable oils, polyethylene glycols and solvents, such as sterile water, alcohols, glycerol and polyhydric alcohols. Intravenous vehicles include fluid and nutrient replenishers. Preservatives include antimicrobial, anti-oxidants, chelating agents and inert gases. Other pharmaceutically acceptable carriers include aqueous solutions, non-toxic excipients, including salts, preservatives, buffers and the like, as described, for instance, in *Remington's Pharmaceutical Sciences,* 15th ed. Easton: Mack Publishing Co., 1405–1412, 1461–1487, 1975, and *The National Formulary XIV.,* 14th ed. Washington: American Pharmaceutical Association, 1975, the contents of which are hereby incorporated by reference. The pH and exact concentration of the various components of the pharmaceutical composition are adjusted according to routine skills in the art. See *Goodman and Gilman's The Pharmacological Basis for Therapeutics,* 7th ed.

In another embodiment, the invention relates to a method of treating a cell proliferative disorder, a disorder associated with oxidative stress, a skin disorder, and a cardiovascular disorder. These methods involves administering to a subject a therapeutically effective dose of a pharmaceutical composition containing the compounds of the present invention and a pharmaceutically acceptable carrier. "Administering" the pharmaceutical composition of the present invention may be accomplished by any means known to the skilled artisan. By "subject" is meant any mammal, preferably a human.

The pharmaceutical compositions are preferably prepared and administered in dose units. Solid dose units are tablets, capsules and suppositories. For treatment of a patient, depending on activity of the compound, manner of administration, nature and severity of the disorder, age and body weight of the patient, different daily doses are necessary. Under certain circumstances, however, higher or lower daily doses may be appropriate. The administration of the daily dose can be carried out both by single administration in the form of an individual dose unit or else several smaller dose units and also by multiple administration of subdivided doses at specific intervals.

The dosage should not be so large as to cause adverse side effects, such as unwanted cross-reactions, anaphylactic reactions and the like. Generally, the dosage will vary with the age, condition, sex, and extent of the disease in the patient and can be determined by one skilled in the art. The dosage can be adjusted by the individual physician in the event of any contraindications and can be readily ascertained without resort to undue experimentation.

The pharmaceutical compositions according to the invention are in general administered topically, intravenously, orally or parenterally or as implants, but even rectal use is possible in principle. Suitable solid or liquid pharmaceutical preparation forms are, for example, granules, powders, tablets, coated tablets, (micro)capsules, suppositories, syrups, emulsions, suspensions, creams, aerosols, drops or injectable solution in ampule form and also preparations with protracted release of active compounds, in whose preparation excipients and additives and/or auxiliaries such as disintegrants, binders, coating agents, swelling agents, lubricants, flavorings, sweeteners or solubilizers are customarily used as described above. The pharmaceutical compositions are suitable for use in a variety of drug delivery systems. For a brief review of present methods for drug delivery, see Langer, *Science*, 242:1527–1533, 1990, which is incorporated herein by reference.

The pharmaceutical compositions according to the invention may be administered locally or systemically. By "therapeutically effective dose" is meant the quantity of a compound according to the invention necessary to prevent, to cure or at least partially arrest the symptoms of the disease and its complications. Amounts effective for this use will, of course, depend on the severity of the disease and the weight and general state of the patient. Typically, dosages used in vitro may provide useful guidance in the amounts useful for in situ administration of the pharmaceutical composition, and animal models may be used to determine effective dosages for treatment of particular disorders. Various considerations are described, e.g., in Gilman et al., eds., *Goodman and Gilman's: the Pharmacological Bases of Therapeutics*, 8th ed., Pergamon Press, 1990; and *Remingon's Pharmaceutical Sciences*, 17th ed, Mack Publishing Co., Easton, Pa., 1990, :each of which is herein incorporated by reference. Effectiveness of the dosage can be monitored methods well known to one of ordinary skill in the art.

Without further elaboration, it is believed that one skilled in the art can, using the preceding description, utilize the present invention to its fullest extent. The following examples are illustrative only, and not limiting of the remainder of the disclosure in any way whatsoever.

EXAMPLES

Example 1

Hesperetin-7-palmitate

A solution of palmitoyl chloride (2.1 mL, 6.9 mmole) in N,N-dimethylacetamide (3 mL) was added dropwise (10 min) to a vigorously stirred suspension containing hesperetin (2 g, 6.6 mmole) and $Na_2CO_3$ (1.1 g) in N,N-dimethylacetamide (15 mL) at 0° C. The mixture, while stirring, was allowed to reach room temperature and then poured to an ice water. The reaction product was extracted with ethyl acetate (60 mL). The organic layer was washed with water, dried over anhydrous $Na_2SO_4$ and the solvent removed under reduced pressure. The crude product was purified using flash chromatography on silica gel with methylene chloride+chloroform (1:1) as the eluent. The final product was crystallized from hexane.

Obtained 2.57 g of hesperetin-7-palmitate (72% of the theoretical yield).

$^1$H-NMR (500 MHz, DMSO-$d_6$) δ: 0.848 (t, J=6.8 Hz, —$CH_2$—$CH_3$), 1.230 (broad, 24H, —$(CH_2)_{12}$—), 1.607 (m, 2H, —$CH_2$—$CH_2$—COO—), 2.547 (t, 2H, J=7.3 Hz, —$CH_2$—COO—), 2.812 (dd, 1H, J=2.9 Hz, J=17.3 Hz, —$C_3$—H), 3.360 (dd, 1H, J=12.7 Hz, J=17.3 Hz, —$C_3$—H), 3.777 (s, 3H, $C_{4'}$—$OCH_3$), 5.557 (dd, 1H, J=2.9 Hz, J=12.7 Hz, $C_2$—H), 6.307 (d, 1H, J=1.8 Hz, $C_6$—H), 6.320 (d, 1H, J=1.8 Hz, $C_8$—H), 6.886 (dd, 1H, J=1.8 Hz, J=8.3 Hz, $C_{6'}$—H), 6.934 (d, 1H, J=1.8 Hz, $C_{2'}$—H), 6.944 (d, 1H, J=8.3 Hz, $C_{5'}$—H), 9.112 (s, 1H, $C_{3'}$—H), 11.938 (s, 1H, $C_5$—OH).

Electrospray spectrum showed: m/z 539 [M−H]

Example 2

Hesperetin-3'-stearate

To a vigorously stirred solution of hesperetin (1 g, 3.31 mmole) in N,N-dimethylacetamide (15 mL) containing sodium carbonate (500 mg) was added dropwise benzyl chloroformate (0.5 mL, 3.5 mmole). The reaction mixture was stirred for 15 min and then poured to an ice water and extracted with ethyl acetate. The organic phase was washed with water, dried over anhydrous sodium sulfate, and the solvent was removed under reduced pressure. The crude product was purified using flash chromatography on silica gel with methylene chloride+chloroform (1:1) and crystallized from ethyl acetate/hexane.

Obtained 0.97 g of hesperetin-7-benzylcarbonate (67% of the theoretical yield).

A solution of stearoyl chloride (0.85 mL, 2.5 mmole) in dioxane (2 mL) was added dropwise to a stirred solution of hesperetin (1 g, 2.29 mmole) and diisopropylethylamine (0.45 ml, 2.6 mmole) in dioxane (10 mL). The reaction mixture was stirred for 30 min, poured into ice water and extracted with ethyl acetate. The organic layer was washed with 1% HCl, water, dried over anhydrous sodium sulfate and the solvent was removed under reduced pressure. The crude product was chromatographed on silica gel with methylene chloride and chloroform as the eluent. In order to cleave benzylformate group at 7-position, the obtained product was dissolved in ethyl acetate and hydrogenated at the presence of 10% palladium on charcoal. After filtration and removal of the solvent the residue was crystallized from hexane.

Obtained 0.62 g of hesperetin-3'-stearate (48% of the theoretical yield).

$^1$H-NMR (500 MHz, DMSO-$d_6$) δ: 0.848 (t, 3H, J=6.7 Hz, —$CH_2$—$CH_3$), 1.229 [broad, 28H, —$(CH_2)_{14}$—], 1.633 (m, 2H, —$CH_2$—$CH_2$—COO—), 2.549 (t, 2H, J=7.3 Hz, —$CH_2$—COO—), 2.728 (dd, 1H, J=2.8 Hz, J=17.0 Hz, $C_3$—H), 3.275 (dd, 1H, J=12.7 Hz, J=17.0 Hz, $C_3$—H), 3.775 (s, 3H, $C_{4'}$—$OCH_3$), 5.515 (dd, 1H, J=2.8 Hz, J=12.7 Hz, $C_2$—H), 5.888 (d, 1H, 1.8 Hz, $C_6$—H), 5.905 (d, 1H, J=1.8 Hz, $C_8$—H), 7.165 (d, 1H, J=8.2 Hz, $C_{5'}$—H), 7.24 (d, 1H, J=2.0 Hz, $C_{2'}$—H), 7.376 (dd, 1H, J=2.0 Hz, J=8.2 Hz, $C_{6'}$—H), 11.800 (broad, 1H, $C_7$—OH), 12.124 (s, 1H, $C_5$—H).

Electrospray mass spectrum showed: m/z 567 [M−H].

Example 3

Hesperetin-7-phosphate and Hesperetin-3'-phosphate

To a stirred solution of hesperetin (300 mg, 0.99 mmole) and phosphorus oxychloride (140μ, 1.5 mmole) in dioxane (3 mL) was added dropwise (15 min) at 0° C. a solution of pyridine (120 μL, 1.5 mmole) in dioxane (1 mL). The reaction mixture was stirred for 15 min at room temperature, and then water (2 mL) was added while stirring was continued for additional 30 min. After this time, the mixture was diluted with water, neutralized to pH 5 with NaHCO$_3$ and extracted with ethyl acetate to remove side products and unreacted hesperetin. The aqueous phase was separated, acidified with HCl to pH 2 and extracted three times with ethyl acetate. The extracts were combined, washed with water dried over anhydrous NaSO$_4$, and the solvent removed under reduced pressure.

The crude product was separated using HPLC on Zorbax C8 column (250×10 mm) with 25% acetonitrile+75% 0.1M (NH$_4$)H$_2$PO$_4$ pH 2.5 adjusted with H$_3$PO$_4$ as the mobile phase, and UV detection at 280 nm. Obtained two fractions with the retention time 8 min and 9 min which correspond to hesperetin-7-phosphate and hesperetin-3'-phosphate, respectively. The fractions with the same retention time were pooled, diluted with water and extracted with ethyl acetate. After evaporation of the solvent, the residue was dissolved in ethanol, neutralized with NaOH to pH 5.5 and the solvent removed under reduced pressure.

Obtained: hesperetin-7-phosphate monosodium salt (180 mg, 45% yield) and hesperetin-3'-phosphate monosodium salt (50 mg, 12% yield)

Spectroscopic data of hesperetin-7-phosphate:
$^1$H-NMR (500 MHz, D$_2$O) δ: 2.783 (dd, 1H, J=2.9 Hz, J=17.3 Hz, C$_3$—H), 3.174 (dd, 1H, J=12.6 Hz, J=17.3 Hz, C$_3$—H), 3.845(s, 3H, C$_{4'}$—OCH$_3$), 5.394 (dd, 1H, J=2.9 Hz, J12.6 Hz, C$_2$—H), 6.344 (d, 1H, J=1.8 Hz, C$_6$—H), 6.382 (d, 1H, J=1.8 Hz, C$_8$—H), 7.021 (s, 2H, C$_{2'}$—H, C$_{6'}$—H), 7.046 (s, 1H, C$_{5'}$—H).
$^{31}$P-NMR (500 MHz, D$_2$O) δ: −0.5642
Electrospray spectrum showed: m/z 381 [M-H].

Spectroscopic data of hesperetin-3'-phosphate:
$^1$H-NMR (500 MHz, D$_2$O) δ: 2.766 (dd, 1H, J=2.5 Hz, 17.3 Hz, C$_3$—H), 3.213 (dd, 1H, J=13.3 Hz, J=17.3 Hz, C$_3$—H), 3.879(s, 3H, C$_{4'}$—OCH$_3$), 5.378 (dd, 1H, J=2.5 Hz, J=13.3 Hz, C$_2$—H), 5.886 (d, 1H, J=1.8 Hz, C$_6$—H), 5.929 (d,1H, J=1.8 Hz, C$_8$—H), 7.078 (d, 1H, J=8.4 Hz C$_{5'}$—H), 7.153 (d, 1H, J=8.4 Hz, C$_{6'}$—H), 7.567 (s, 1H, C$_{2'}$—H).
$^{31}$P-NMR (500 MHz, D$_2$O) δ: 0.4697
Electrospray spectrum showed: m/z 381 [M-H].

Although the invention has been described with reference to the presently preferred embodiment, it should be understood that various modifications can be made without departing from the spirit of the invention. Accordingly, the invention is limited only by the following claims.

What is claimed is:

1. A hydrophilic hesperetin pro-form of the formula

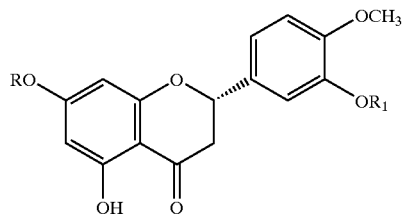

wherein:

R is an —H—, and R$_1$ is selected from the group consisting of an organic phosphoric acid salt, an organic sulfuric acid salt, an inorganic phosphoric acid salt and an inorganic sulfuric acid salt, or R$_1$ is an —H— and R is selected from the group consisting of an organic phosphoric acid salt, an organic sulfuric acid salt, an inorganic phosphoric acid salt and an inorganic sulfuric acid salt.

2. A pharmaceutical composition suitable for topical or oral administration in an individual, said composition comprising a hydrophilic hesperetin pro-form and a pharmaceutically acceptable carrier, wherein said hesperetin pro-form has the formula:

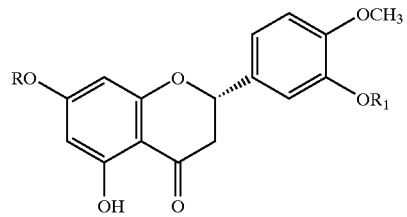

wherein:

R is an —H—, and R$_1$ is selected from the group consisting of an organic phosphoric acid salt, an organic sulfuric acid salt, an inorganic phosphoric acid salt and an inorganic sulfuric acid salt, or R$_1$ is an —H— and R is selected from the group consisting of an organic phosphoric acid salt, an organic sulfuric acid salt, an inorganic phosphoric acid salt and an inorganic sulfuric acid salt.

3. The hydrophilic hesperetin pro-form of claim 1, wherein R is an —H—, and R$_1$ is selected from the group consisting of an organic phosphoric acid salt or an inorganic phosphoric acid salt, or R$_1$ is an —H— and R is selected from the group consisting of an organic phosphoric acid salt or an inorganic phosphoric acid salt.

4. The hydrophilic hesperetin pro-form of claim 3, wherein R is an —H—, and R$_1$ is an organic phosphoric acid salt, or R$_1$ is an —H— and R is an organic phosphoric acid salt.

5. The hydrophilic hesperetin pro-form of claim 3, wherein R is an —H—, and R$_1$ is an inorganic phosphoric acid salt, or R$_1$ is an —H— and R is an inorganic phosphoric acid salt.

6. The pharmaceutical composition of claim 2, wherein R is an —H—, and R$_1$ is selected from the group consisting of an organic phosphoric acid salt or an inorganic phosphoric acid salt, or R$_1$ is an —H— and R is selected from the group consisting of an organic phosphoric acid salt or an inorganic phosphoric acid salt.

7. The pharmaceutical composition of claim 6, wherein R is an —H—, and R$_1$ is an organic phosphoric acid salt, or R$_1$ is an —H— and R is an organic phosphoric acid salt.

8. The pharmaceutical composition of claim 6, wherein R is an —H—, and R$_1$ is an inorganic phosphoric acid salt, or R$_1$ is an —H— and R is an inorganic phosphoric acid salt.

* * * * *